United States Patent [19]
Arai et al.

[11] Patent Number: 5,510,082
[45] Date of Patent: Apr. 23, 1996

[54] CHEMICAL ANALYSIS FILM SUPPLIER

[75] Inventors: Kenji Arai, Kanagawa; Masaaki Terashima, Saitama; Yoshiyuki Doi, Kanagawa, all of Japan

[73] Assignee: Fuji Photo Film Co., Ltd., Kanagawa, Japan

[21] Appl. No.: 324,987

[22] Filed: Oct. 18, 1994

[30]   Foreign Application Priority Data

Oct. 25, 1993 [JP] Japan .................................. 5-266182
Apr. 15, 1994 [JP] Japan .................................. 6-077334

[51] Int. Cl.$^6$ ................................................ G01N 37/00
[52] U.S. Cl. .................... 422/64; 422/63; 422/67; 422/104; 422/119; 436/43; 436/46; 436/50
[58] Field of Search ............................. 422/63, 64, 65, 422/66, 67, 99, 104, 105, 108, 119, 58; 436/43, 44, 46, 47, 48, 50, 55, 174; 364/497, 500

[56]        References Cited

U.S. PATENT DOCUMENTS

| | | | |
|---|---|---|---|
| 4,451,443 | 5/1984 | Yamashita et al. | 422/63 |
| 4,455,280 | 6/1984 | Shinohara et al. | 422/63 |
| 4,512,952 | 4/1985 | Blanding et al. | 422/63 |
| 4,807,984 | 2/1989 | Kurimura et al. | 350/529 |
| 5,043,143 | 8/1991 | Shaw et al. | 422/65 |
| 5,051,238 | 9/1991 | Umetsu et al. | 422/64 |
| 5,075,079 | 12/1991 | Kerr et al. | 422/64 |
| 5,077,010 | 12/1991 | Ishizaka et al. | 422/56 |
| 5,089,418 | 2/1992 | Shaw et al. | 436/46 |
| 5,102,624 | 4/1992 | Muraishi | 422/64 |
| 5,169,600 | 12/1992 | Ishizaka et al. | 422/66 |

FOREIGN PATENT DOCUMENTS 0064691  11/1982  European Pat. Off. .
0555654  8/1993   European Pat. Off. .

Primary Examiner—James C. Housel
Assistant Examiner—Long V. Le
Attorney, Agent, or Firm—Sughrue, Mion, Zinn, Macpeak & Seas

[57]        ABSTRACT

A plurality of dry chemical analysis films are stacked in a cartridge. A chemical analysis film supplier has a cartridge storage chamber in which a plurality of cartridges are stored so that the chemical analysis films in each cartridge can be taken out by a chemical analysis film removing device. In the the cartridge storage chamber, the cartridges are arranged in a circle, and a moisture-absorber holding portion is formed inside the circle of the cartridges, and a moisture absorber is loaded in the moisture-absorber holding portion.

6 Claims, 12 Drawing Sheets

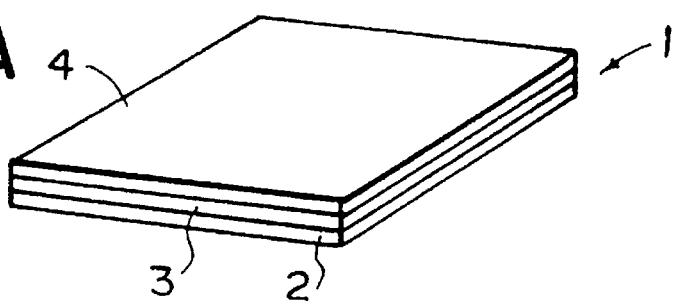
F I G. 2A
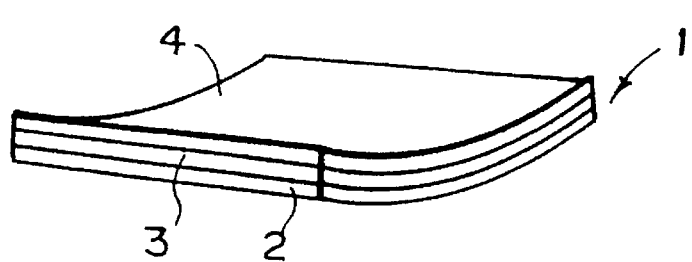
F I G. 2B
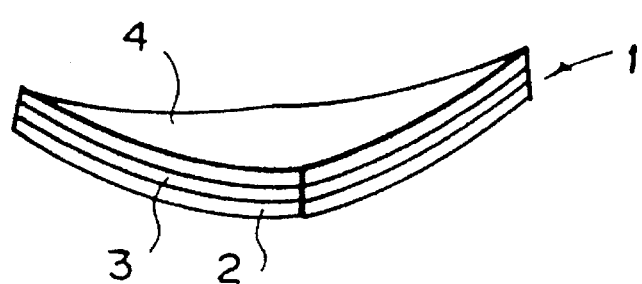
F I G. 2C

CHEMICAL ANALYSIS FILM SUPPLIER

BACKGROUND OF THE INVENTION

1. Field of the Invention

This invention relates to a chemical analysis film supplier for supplying, in a biochemical analysis apparatus, chemical analysis films each having a reagent layer containing a reagent whose optical density changes through a chemical reaction, a biochemical reaction, an immunoreaction or the like with a specific biochemical component contained in a sample liquid such as blood or urine.

2. Description of the Prior Art

There has been put into practice a "dry-to-touch" chemical analysis film with which the content of a specific chemical component contained in a sample liquid, the activity thereof or the content of a solid component can be quantitatively analyzed by only spotting a droplet of the sample liquid on the film. As such a dry chemical analysis film, there has been known an integrated multi-layered chemical analysis film (sometimes referred to as "multi-layered chemical analysis element") comprising a support sheet of organic polymer and at least one reagent layer which contains a reagent and is formed on the support sheet. A spreading layer is sometimes provided over the reagent layer. Further a dry chemical analysis element which is formed of filter paper and has one or more layers has been proposed and partly put into practice.

When quantitatively analyzing the chemical components or the like contained in a sample liquid using such a dry chemical analysis film, a droplet of the sample liquid is spotted on the film (on the spreading layer when the film is provided with a spreading layer and on the reagent layer when the film is not provided with a spreading layer) and is held at a constant temperature for a predetermined time (incubation) in an incubator so that coloring reaction occurs, and the optical density of the color formed by the coloring reaction is optically measured. That is, measuring light containing a wavelength which is pre-selected according to the combination of the component to be analyzed and the reagent contained in the reagent layer of the film is projected onto the film and the optical density of the film is measured. Then the concentration or the activity of the component to be analyzed is determined on the basis of the optical density using a calibration curve which represents the relation between the concentration of the biochemical component and the optical density.

The integrated multi-layered chemical analysis film is generally in the form of a film chip of a predetermined shape such as square or rectangle. The film chip is sometimes provided with a frame of organic polymer for facilitating automated handling of the chemical analysis film and is used in the form of a chemical analysis slide. In a biochemical analysis apparatus we have proposed previously, the film chip is used at it is without frame (will be referred to as "frameless chemical analysis film", hereinbelow). A plurality of the frameless chemical analysis films are loaded in a cartridge and the cartridge is loaded in a chemical analysis film supplier for a biochemical analysis apparatus. The frameless chemical analysis films are taken out from the cartridge in the supplier one by one.

In the biochemical analysis apparatus, a plurality of cartridges containing therein different chemical analysis films are loaded in a chemical analysis film supplier and the chemical analysis films are taken out one by one from a cartridge selected according to the item of measurement. For example, in the chemical analysis film supplier disclosed in Japanese Unexamined Patent Publication 59(1984)-20858, U.S. Pat. No. 4,512,952, U.S. Pat. No. 5,089,418 or the like, the cartridges are arranged in a circle on a rotary support in the chemical analysis film supplier and the support is rotated to bring a selected cartridge to a film take-out mechanism, which is arranged to push out a chemical analysis film from the cartridge by a sliding member which slides from the inside out.

In order to maintain the performance of the dry chemical analysis films to ensure accuracy of measurement, the films should be stored in the chemical analysis film supplier at a humidity in a predetermined range. That is, the chemical analysis film contains biochemical materials such as enzymes, antibodies and the like selected according to the item of the measurement and generally it is preferred that the chemical analysis films be stored at a low humidity so that initiation of reaction is suppressed. Some chemical analysis films, e.g., those for determining total protein (TP), high density lipoprotein-cholesterol (HDL-C), albumin (ALB) or the like, should be stored under a different humidity condition, i.e., in a range somewhat above 0% RH.

As disclosed in Japanese Unexamined Utility Model Publication No. 5(1993)-33048 (U.S. Pat. No. 5,043,143), there has been proposed a technique in which a first chamber containing therein a moistening means such as a sponge member soaked with water and a second chamber containing therein a dehumidifying means such as a drying agent are provided to communicate with the bottom of a film storage chamber in which the chemical analysis films are stored, and the humidity in the film storage chamber is controlled by causing the film storage chamber to communicate selectively with the first or second chamber.

However, the chemical analysis film supplier in accordance with the technique is disadvantageous in that since the driving mechanism for taking out the dry chemical analysis films from the cartridges arranged in a circle is disposed at the center of the chemical analysis film supplier, the space for accommodating a moisture-absorptive agent (dehydrating agent or humidity conditioning agent) for keeping the chemical analysis films under a predetermined humidity condition must be disposed below or outside the film storage chamber, which makes it troublesome to change the moisture-absorptive agent, makes it difficult to reduce the size of the chemical analysis film supplier and adds to the cost.

Especially when a plurality of cartridges are to be stored under different humidity conditions, the space for storing the cartridges must be partitioned into a plurality of film storage chambers and a moisture-absorptive agent (dehydrating agent or moisture conditioning agent) must be provided for each of the film storage chambers, which further complicates the structure in the chemical analysis film supplier and makes it further troublesome to change the moisture-absorptive agent.

Further the conventional chemical analysis film supplier generally comprises a container which can keep the atmosphere therein at a low humidity and a cartridge holding member which is provided with a plurality of cartridge holding portions and is supported in the container so that the cartridge holding member is movable relative to the container to bring the cartridge held in each of cartridge holding portions to a film takeout port formed in the container. The cartridges are put in the container body through a cartridge inlet-outlet port formed in the container. This arrangement gives rise to the following problem.

That is, sometimes it is necessary to transfer all the cartridges in the chemical analysis film supplier to another place held at a low temperature and a low humidity such as in a refrigerator, for instance, when the chemical analysis film supplier fails or is to be maintained, or when the chemical analysis film stored therein is not to be used for a predetermined time interval. When the cartridges are unloaded from the chemical analysis film supplier, all the cartridges in the supplier must be taken out one by one through the cartridge inlet-outlet port and when the cartridges are reloaded in the chemical analysis film supplier, the cartridges must be inserted into the supplier one by one through the cartridge inlet-outlet port. This is a very troublesome work. Further, it is preferred that each cartridge unloaded from the supplier be returned to the same cartridge holding portion. For this purpose, the cartridges must be unloaded and reloaded while checking the relation between the cartridges and the cartridge holding portions. This operation is not only very troublesome but also apt to lead an error in positioning the cartridges.

The problem described above is true of a chemical analysis film supplier where the chemical analysis films are directly loaded in film holding portions of a film holding member in the supplier without use of cartridge.

SUMMARY OF THE INVENTION

In view of the foregoing observations and description, the primary object of the present invention is to provide a chemical analysis film supplier in which a plurality of cartridges are arranged in a circle and the moisture-absorptive agent for keeping the chemical analysis films in the supplier under a predetermined humidity condition can be easily changed.

Another object of the present invention is to provide a chemical analysis film supplier in which the chemical analysis film in the chemical analysis film supplier can be easily transferred from the supplier and easily returned to the supplier.

In a first aspect of the present invention, there is provided a chemical analysis film supplier in which a plurality of chemical analysis film cartridges each containing therein a plurality of dry chemical analysis films are stored in a cartridge storage chamber so that the chemical analysis films in each cartridge can be taken out by a chemical analysis film take-out means, wherein the improvement comprises that the cartridges are arranged in a circle, a moisture-absorber holding portion is formed inside the circle of the cartridges and a moisture absorber is loaded in the moisture-absorber holding portion.

In the chemical analysis film supplier of the first aspect, since the cartridges are arranged in a circle and the chemical analysis films are taken out by a chemical analysis film take-out means, the moisture-absorber holding portion can be formed inside the circle of the cartridges, whereby the moisture absorber can be easily changed, for instance, from above and the film supplier can be compact in size.

In a second aspect of the present invention, there is provided a chemical analysis film supplier in which a plurality of chemical analysis film cartridges each containing therein a plurality of dry chemical analysis films are stored in a cartridge storage chamber so that the chemical analysis films in each cartridge can be taken out by a chemical analysis film take-out means, wherein the improvement comprises that the cartridges are arranged in a plurality of concentric circles, the cartridge storage chamber is partitioned into inner and outer chambers, the cartridges arranged in one or more inner circles being positioned in the inner chamber and the other cartridges being positioned in the outer chamber, an inner moisture-absorber holding portion in which a first moisture-absorber is loaded is formed inside the circles of the cartridges in the inner chamber while an outer moisture-absorber holding portion in which a second moisture-absorber is loaded is formed outside the outer chamber.

In the chemical analysis film supplier of the second aspect, since the cartridge storage chamber is partitioned into inner and outer chambers and the moisture-absorber holding portion for the inner chamber is formed inside the inner chamber and that for the outer chamber is formed outside the outer chamber, an arrangement of a film supplier for storing the cartridges under different humidity conditions can be easily obtained with a compact structure.

It is preferred that the moisture-absorber be loaded in the moisture-absorber holding portion from above.

As the moisture absorber, drying agents, humidity conditioning agents, humidity condition devices or the like can be used.

In accordance with a third aspect of the present invention, there is provided a chemical analysis film supplier for a biochemical analysis apparatus in which a plurality of dry chemical analysis films are held in a plurality of film holding portions formed in a film holding member and stored in a container so that the chemical analysis films can be taken out from each film holding portions, wherein the improvement comprises that the film holding member is able to be removed from the container and to be returned to the container while carrying thereon the chemical analysis films held in the film holding portions.

The chemical analysis films may be directly loaded in the film holding portions or cartridges each containing therein a plurality of chemical analysis films may be loaded in the film holding portions.

The film supplier of the third aspect may be arranged so that the film holding member can be moved relative to the container to bring each film holding portion or the chemical analysis films held therein to a film takeout port formed in the container. In this case, it is preferred that the driving mechanism for moving the film holding member be arranged to be disengaged from the film holding member when the film holding member is removed from the container and to be engaged with the film holding member when the film holding member is loaded in the container so that the film holding means can be driven.

Further it is preferred that a moisture-absorber be loaded in the container, the moisture-absorber being removable from the container together with the film holding member.

Preferably the film supplier of the third aspect is provided with an indicating system which judges whether the chemical analysis films in the film holding portions in the film holding member returned to the container are still usable and indicates the result of the judgement.

For example, whether the cartridge or the chemical analysis film therein is still usable can be judged on the basis of the age of the cartridge, i.e., the time which elapses from the time the cartridge is first put in the container. The age of the cartridge may be determined taking into account the condition under which the cartridge is kept. That is, the service life of each cartridge is determined in advance in terms of the period for which the cartridge (or the chemical analysis films therein) will be usable when the cartridge is kept in the container throughout its life. Accordingly, when the cartridge is once taken out from the container and is kept under a condition different from the condition in the container, the age of the cartridge is expressed in terms of the age when the cartridge is kept in the container (effective age). Then the effective age of the cartridge is compared with a reference time determined on basis of the service life of each cartridge. For this purpose, the absent time for which the cartridge is absent from the container is calculated and is converted into an effective aging period on the basis of a correction value. The correction value for each cartridge is determined on the basis of the difference between the rate of deterioration with age of the chemical analysis films in each cartridge when the cartridge is kept in the container and that when the cartridge is kept under a different condition such as in a refrigerator.

In the chemical analysis film supplier of the third aspect, the chemical analysis films or the cartridges are unloaded from and reloaded in the container together with the film holding member with the chemical analysis films or the cartridges held in the film holding portions.

Accordingly, the chemical analysis films or the cartridges can be easily unloaded and reloaded in a short time without checking the relation between the chemical analysis films (or the cartridges) and the film holding portions.

Further when said indicating means is provided, use of deteriorated chemical analysis films can be avoided in the biochemical analysis.

BRIEF DESCRIPTION OF THE DRAWINGS

FIGS. 2A to 2C are views showing a chemical analysis film in different states.

DESCRIPTION OF THE PREFERRED EMBODIMENTS

Figure 1:
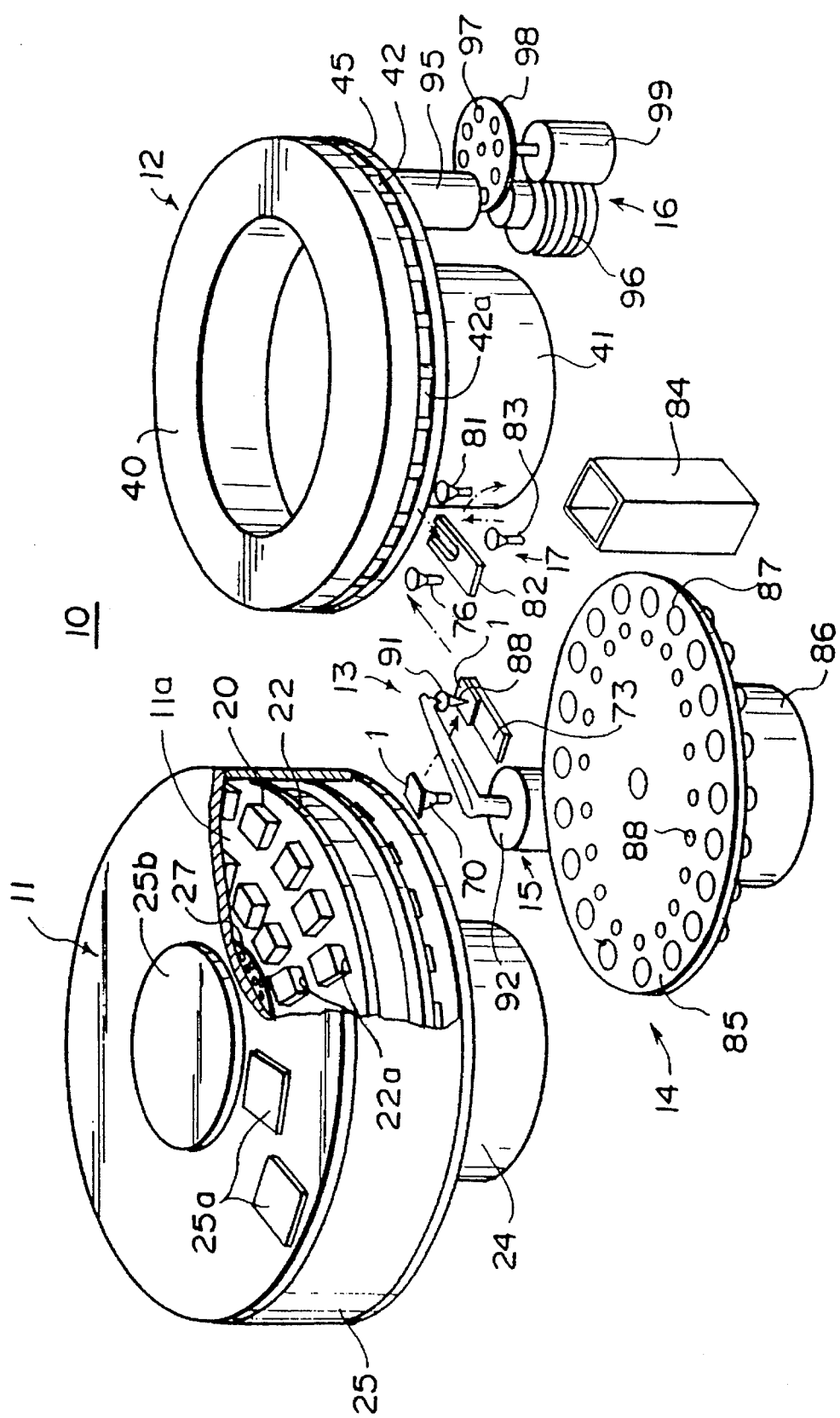
FIG. 1 is a schematic perspective view of a biochemical analysis apparatus provided with a chemical analysis film supplier in accordance with an embodiment of the present invention.

In FIG. 1, a biochemical analysis apparatus 10 comprises a chemical analysis film supplier 11 in accordance with an embodiment of the present invention loaded with a plurality of cartridges 20 each containing therein a stack of a plurality of virgin chemical analysis films (frameless chemical analysis films) 1, an incubator 12 which is disposed beside the film supplier 11 and incubates the films 1 transferred from the film supplier 11 for a predetermined time at a predetermined temperature, a film transfer means 13 which transfers the film 1 from the film supplier 11 to the incubator 12, a sample liquid supplier 14 in which a plurality of sample liquids such as serum, urine or the like are stored, a spotting means 15 which applies one of the sample liquids in the sample liquid supplier 14 to the film chips 1 on the way to the incubator 12, and a measuring means 16 disposed below the incubator 12.

FIG. 2A shows the chemical analysis film 1 and FIGS. 2B and 2C show the chemical analysis film 1 in a dry state. As shown in FIGS. 2A to 2C, the chemical analysis film 1 is formed by coating or bonding a reagent layer 3 on a transparent support sheet 2 of an organic polymer sheet or the like (e.g., polyethylene terephthalate sheet or polystyrene sheet), and laminating a spreading layer 4 on the reagent layer 3. In this embodiment, the chemical analysis film 1 is not provided with any frame.

The reagent layer 3 comprises at least one layer composed of a porous layer or a hydrophilic polymer binder such as gelatin containing therein a reagent component which selectively reacts with a predetermined analyte and a reagent component necessary for coloring reaction (chemical analysis reagent or immunoassay reagent).

The spreading layer 4 is formed of woven or knitted fabric (or cloth) of synthetic fiber resistant to rubbing such as polyester, or of blend of natural fiber and synthetic fiber, unwoven fabric or paper and functions as a protective layer. Further the spreading layer 4 causes sample liquid applied thereto to uniformly spread over the reagent layer 3.

Under the normal humidity conditions the film 1 is substantially flat as shown in FIG. 2A. The film 1 is stored in a dry environment (e.g., in an environment where the humidity is not higher than 20%) in order to suppress chemical reaction, and in a dry state, the film 1 is warped (curled or curved) toward the spreading layer 4 as shown in FIG. 2B or 2C.

The frameless chemical analysis films 1 are stored in cartridges 20 (FIG. 3) for the respective items of analysis. In the cartridge 20, a plurality of the frameless chemical analysis films 1 are stacked with the support sheets 2 facing downward. As shown in FIG. 1, the film supplier 11 is provided with a plurality of cartridge holding portions 22a which are arranged in inner and outer circles on a disk-like support 22 and a plurality of cartridges 20 loaded with the frameless chemical analysis films 1 are held in the respective cartridge holding portions 22a. The support 22 is supported for rotation on a base portion 24 and is rotated by a supplier motor not shown so that a predetermined cartridge holding portion 22a is brought to a film takeout position where the film transfer means 13 takes out a frameless chemical analysis film 1 from the cartridge 20.

The support 22 is provided with a cover 25 which encloses the inner space (the film storage chamber) 11a of the film supplier 11. A pair of openings 25a having lids are provided in the upper wall of the cover 25 and the cartridges 20 are taken out and inserted into the cartridge holding portions 22a through the openings 25a. A moisture-absorptive agent holding portion 27 is formed in the support 22 at the center thereof and moisture-absorptive agent is loaded in the moisture-absorptive agent holding portion 27 through an opening 25*b* formed in the cover 25. The opening 25*b* is provided with a lid and the moisture-absorptive agent holding portion 27 is communicated with the film storage chamber 11*a* to permit circulation of air between the moisture-absorptive agent holding portion 27 and the film storage chamber 11*a*. Thus the film storage chamber 11*a* of the film supplier 11 is kept at a low humidity in a predetermined humidity range.

As the moisture-absorptive agent, for instance, drying agents such as silica gel, molecular sieves, activated china clay and activated alumina, these drying agents added with a predetermined amount of water, humidity conditioning agents obtained by adding a predetermined concentration of lithium chloride, potassium acetate or glycerin to the drying agents can be used. The film storage chamber 11*a* is kept at a humidity about 0% RH or a predetermined humidity range above 0% RH.

A shutter (not shown) is provided in the lower surface of the cover 25 in the film takeout position. The shutter is opened when the frameless chemical analysis film 1 is taken out from the cartridge 20 and a suction pad 70 of the film transfer means 13 takes out the lowermost film 1 in the cartridge 20 through the shutter.

Figure 3A:
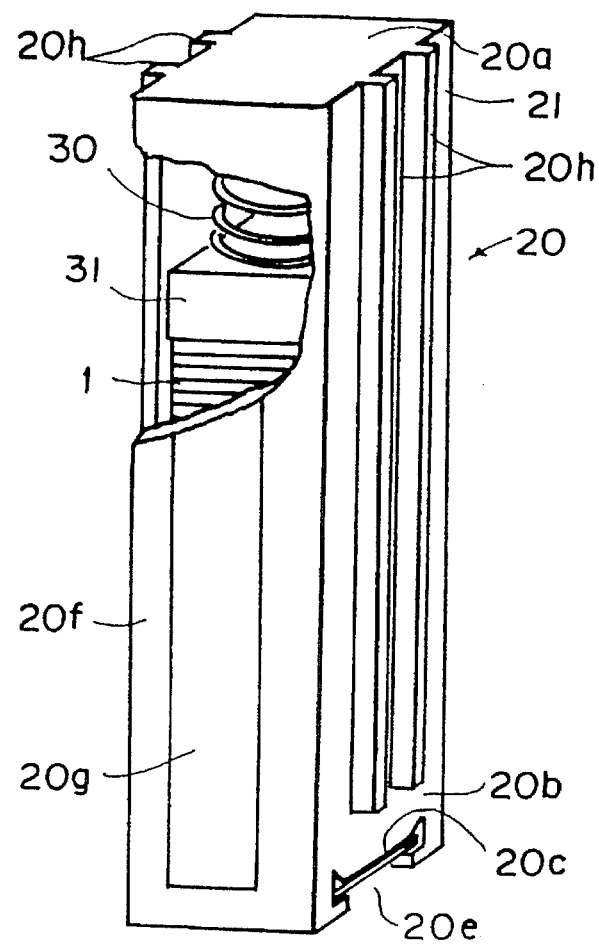
FIG. 3A is a perspective view partly cut away showing a chemical analysis film cartridge.
Figure 3B:
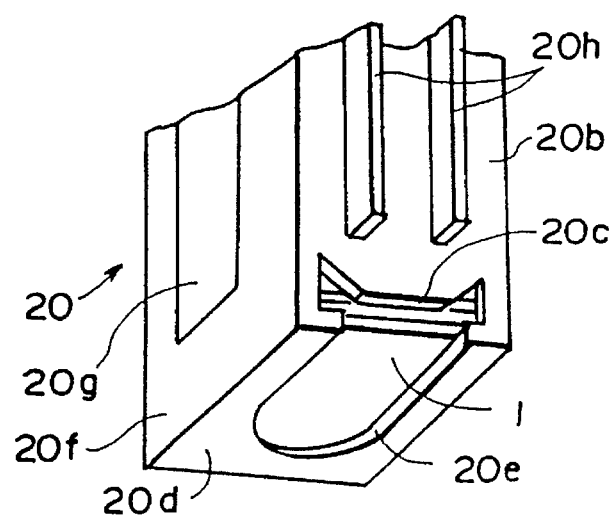
FIG. 3B is a fragmentary perspective showing a bottom portion of the cartridge.

As shown in FIGS. 3A and 3B, the cartridge 20 comprises a box-like casing 21 for accommodating a stack of chemical analysis films 1, a spring member 30 mounted on the inner side of the top wall 20*a* of the casing 21 and a pushing member 31 which is mounted on the lower end portion of the spring member 30 and urges downward the stack of the films 1. A first opening 20*c* is formed in one side wall 20*b* of the casing 21 at a portion near to the bottom wall 20*d* of the casing 21. The first opening 20*c* is shaped and sized to permit only the lowermost film of the stack to pass therethrough. A U-shaped second opening 20*e* which gives a suction pad 70 (FIG. 1) for taking out the film 1 access to the lowermost film 1*a* is formed in the bottom wall 20*d* of the casing 21.

On the outer surface of another side wall 20*f* of the casing 21, there is provided magnetic stripes (or a magnetic band) 20*g* which carries information such as properties of the films 1 in the cartridge 20. A pair of ribs 20*h* are formed in each of the side wall 20*b* and the side wall opposite to the side wall 20*b* in order to hold the cartridge 20 in the cartridge holding portion 22*a* and to prevent insertion of the cartridge 20 in a wrong position.

The incubator 12 comprises a disk-like body portion 40 which is supported to be rotated by a drive mechanism 41 disposed below the body portion 40 at the center thereof. A plurality of cells 42 are provided in the body portion 40 at predetermined intervals in the circumferential direction thereof. The chemical analysis films 1 are incubated in the cells 42.

The body portion 40 comprises a lower disk 45 of metal having a flat upper surface and an upper disk of metal (not shown) provided on the lower disk 45. The peripheral edge portion of the upper disk is bulged upward to form an annular channel open downward. The lower edge of the outer peripheral edge of the upper disk is spaced from the upper surface of the lower disk 45 to form an opening 42*a* which opens in the side surface of the incubator 12 and gives access to the cells 42. A heater (not shown) is disposed between the lower and upper disks. The heater is controlled to heat the chemical analysis films 1 in the cells 42 to a predetermined temperature (e.g., 37° C.).

A plurality of light measuring windows for photometry are formed in the lower disk 45 to be opposed to the respective cells 42, and a film retainer for fixing the chemical analysis film 1 in a predetermined position in the cell 42 is provided in each of the cells 42. A measuring system 16 has a light measuring head 95 which is disposed below the body portion 40 in a light measuring position.

The film transfer means 13 for transferring the film 1 from the film supplier 11 to the incubator 12 comprises said suction pad 70 for taking out the film 1 from the cartridge 20, a horseshoe-like transfer member 73 which receives the film 1 held on the suction pad 70 from below the film 1 with the reagent layer 3 facing upward and inserts the film 1 into the cell 42 in the incubator 12 through the opening 42*a* which opens sideways, and a suction member 76 which moves in and out the cell 42 from below the cell and receives the film 1 held by the transfer member 73 inside the cell 42.

The suction pad 70 is moved up and down and back and forth by a drive mechanism (not shown) to take out the film 1 from the cartridge 20 and transfer the film 1 to the position where the sample liquid is applied on the film 1. The suction member 76 is positioned below the cell 42 in the incubator 12 and is moved up and down by a drive mechanism (not shown) into and away from the cell 42 through the light measuring window.

A film discharge means 17 is disposed in the film discharge position of the incubator 12. The film discharge means 17 comprises a suction pad 81 which attracts the film 1 in the cell 42 which has finished with measurement and lifts it, a horseshoe-like transfer member 82 which receives the film 1 from the suction pad 81 and transfers it outside the incubator 12 and a discarding suction pad 83 which receives the film 1 from the transfer member 82 and discards it into a discarding box 84.

The sample liquid supplier 14 comprises a turn table 85 which is rotated by a drive mechanism 86. The turn table 85 holds a plurality of sample tubes 87 filled with sample liquids which are arranged along the circumferential edge of the turn table 85 and is rotated to bring the sample tubes 87 to a sample liquid supplying position one by one. A plurality of nozzle tips 88 which are mounted on a spotting nozzle 91 to be described later are held on the turn table 85 inside the sample tubes 87.

The spotting means 15 for applying the sample liquid to the film 1 comprises a spotting nozzle 91 which sucks and discharges the sample liquid, and a nozzle tip 88 like a pipette is demountably mounted on the nozzle 91. The nozzle 91 is moved up and down and rotated by a drive mechanism 92. That is, the nozzle 91 sucks the sample liquid from the sample liquid supplier 14, is moved to the film 1 held by the transfer member 73, and then applies the sample liquid to the film 1. The nozzle tip 88 is changed every time the sample liquid is changed.

The film 1 applied with the sample liquid is transferred to the incubator 12 and incubated there. After incubation for a predetermined time, the optical density of the reagent layer 3 is measured by the light measuring system 16 disposed below the incubator 12. The light measuring system 16 comprises said light measuring head 95 for measuring the optical density of the color formed by the coloring reaction between the reagent layer 3 and the analyte in the sample liquid. The light measuring head 95 projects measuring light containing light of a predetermined wavelength onto the reagent layer 3 through the support sheet 2 and detects reflected light with a photodetector. Light from a light source (lamp) 96 enters the light measuring head 95 through an interference filter 97 and is caused to impinge upon the reagent layer 3 by the head 95. A plurality of kinds of the filters 97 are mounted on a rotary disk 98 which is driven by an electric motor 99 and one of the filters 97 is selected according to the item of measurement. A diffraction grating may be used instead of the interference filter 97 as a spectral means employed in the optical system for projecting the measuring light.

The reflected light from the reagent layer 3 carries thereon optical information (more particularly the amount of light) on the amount of coloring substances formed by the coloring reaction between the reagent layer 3 and the sample liquid. The reflected light is received by the photodetector and the optical information carried by the reflected light is converted to an electric signal by the photodetector. The electric signal is input into a determination section through an amplifier. The determination section determines the optical density of the coloring substances formed by the coloring reaction between the reagent layer 3 and the sample liquid on the basis of the level of the electric signal and determines the concentration or the activity of a predetermined biochemical component in the sample liquid by colorimetry.

The measurement by the biochemical analysis apparatus 10 is effected in the following manner. That is, a film 1 is taken out by the suction pad 70 of the transfer means 13 from a cartridge 20 (in the film supplier 11) storing therein chemical analysis films 1 corresponding to the item of measurement at a predetermined humidity. The film 1 held by the suction pad 70 is transferred to the transfer member 73 with the reagent layer 3 facing upward and a sample liquid is applied to the reagent layer 3.

That is, a nozzle tip 88 is mounted on the spotting nozzle 91 of the spotting means 15 and the spotting nozzle 91 is moved above a desired sample tube 87 in the sample liquid supplier 14. Then the nozzle 91 is moved downward to bring the nozzle tip 88 into the sample liquid and the nozzle 91 sucks a predetermined amount of the sample liquid into the nozzle tip 88. Thereafter the nozzle 91 is moved above the center of the film 1 on the transfer member 73 and moved downward toward the film 1, where a predetermined amount of sample liquid is applied to the reagent layer 3 from the nozzle tip 88. The sample liquid spreads over the reagent layer 3 and mixes with the reagent therein.

The film 1 applied with the sample liquid is inserted into one of the cells 42 of the incubator 12 through the side opening 42a by the transfer member 73.

Coloring reaction (coloring substance forming reaction) is caused when the film 1 with the sample liquid is heated to a predetermined temperature in the enclosed cell 42 in the incubator 12, and the optical density of the coloring substances is measured by the light measuring head 95 after a predetermined time or at predetermined intervals.

A more concrete embodiment of the chemical analysis film supplier will be described with reference to FIGS. 4 and 5, hereinbelow.

Figure 4:
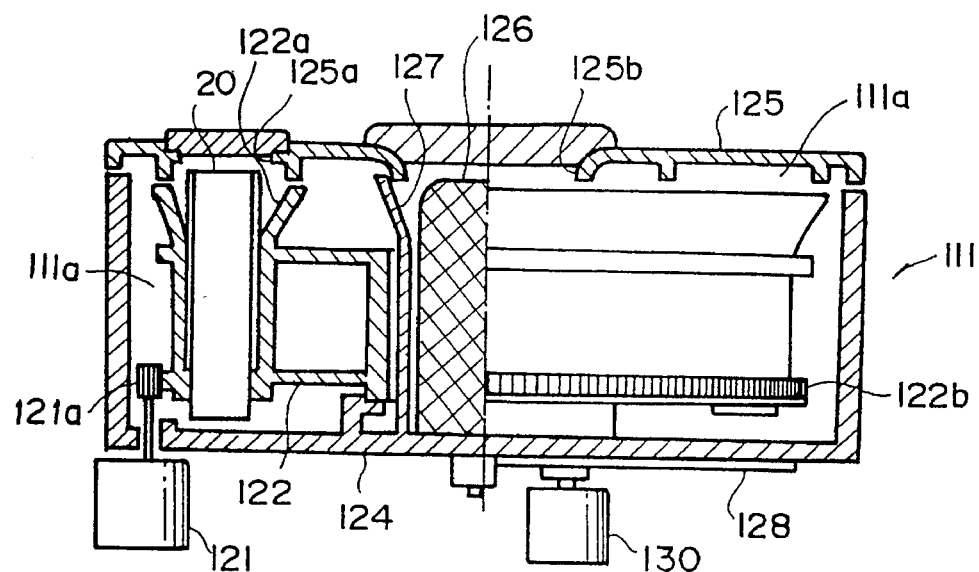
FIG. 4 is a schematic cross-sectional view showing a film supplier in accordance with an embodiment of the present invention.
Figure 5:
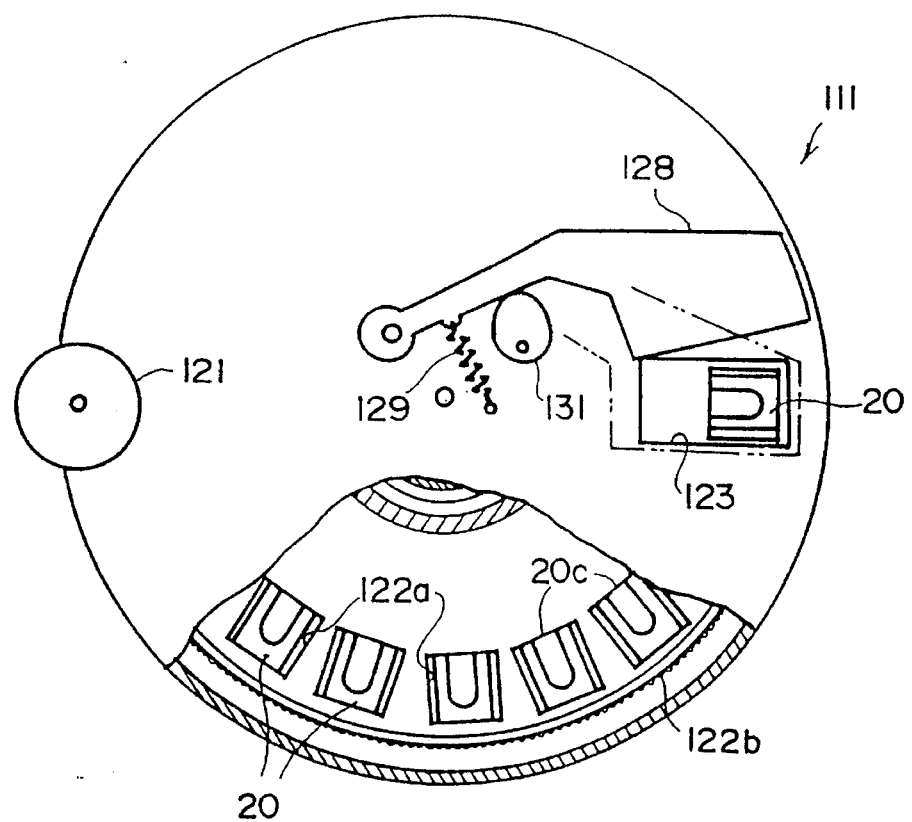
FIG. 5 is a bottom view partly cut away of the film supplier shown in FIG. 4, FIGS. 6A to 6D are schematic views for illustrating the procedure of taking out the film from the cartridge.

In FIGS. 4 and 5, the chemical analysis film supplier 111 of this embodiment is substantially the same as the film supplier 11 shown in FIG. 1 in structure. That is, the film supplier 111 comprises a disk-like support 122 supported for rotation on a base portion 124. In this embodiment, a plurality of cartridge holding portions 122a are arranged in a circle on the disk-like support 122. A plurality of cartridges 20 are held in the respective cartridge holding portions 122a.

The support 122 is provided with a cover 125 which tightly encloses the inner space (film storage chamber) 111a of the film supplier 111. The cover 125 is provided with an opening 125a provided with lids and the cartridges 20 can be taken out and inserted into the cartridge holding portions 122a through the opening 125a. The cover 125 can be removed from the base portion 124, and in the case where trouble occurs in the film supplier 111 and the cartridges 20 are to be transferred to other place, the cover 125 is removed from the base portion 124 so that the cartridges 20 can be taken out quickly.

A moisture-absorptive agent holding portion 127 is formed in the support 122 at the center thereof and a moisture-absorptive agent 126 is loaded in the moisture-absorptive agent holding portion 127 through an opening 125b formed in the cover 125 at the center thereof. The opening 125b is provided with a lid. Thus the inner space of the film storage chamber 111a is kept in a predetermined humidity range.

A film takeout port 123 for taking out a predetermined film 1 from the cartridge 20 is formed in the bottom wall of the base portion 124 and a shutter 128 for opening and closing the port 123 is provided. The shutter 128 is urged by a spring 129 toward a closing position in which it closes the port 123 and is driven to an open position where it opens the port 123 by a cam 131 which is rotated by a shutter motor 130. Teeth 122b are formed on the peripheral surface of the support 122 and are in mesh with a gear 121a fixed to the output shaft of a support motor 121. The support 122 is rotated by the support motor 121 so that a predetermined one of the cartridge holding portions 122a is brought to a film takeout position opposed to the film takeout port 123.

As shown in FIGS. 6A to 6D, a film takeout means 113 is provided below the film takeout port 123 to take out the chemical analysis film 1 from the cartridge 20 in the film takeout position.

As shown in FIGS. 6A to 6D, the film takeout means 113 comprises a base portion 114, a suction pipe 115 mounted on the base portion 114, a suction pad 170 connected to the suction pipe 115, a guide member 116 mounted on the suction pipe 115 to be movable up and down relative to the suction pipe 115, and a drive mechanism not shown. A coil spring 117 is provided on the suction pipe 115 between the guide member 116 and the base portion 114, and the suction pipe 115 is connected to a suction pump (not shown) through the base portion 114.

The cartridge 20 is held in each cartridge holding portion 122a with a predetermined play. That is, the inner size of the cartridge holding portion 122a as measured in the circumferential direction of the support 122 is larger than the outer size of the cartridge 20 as measured in the circumferential direction of the support 122 by a predetermined length (i.e., the sum of L and M in FIG. 6A) and the inner size of the cartridge holding portion 122a as measured in the radial direction of the support 122 is substantially equal to the outer size of the cartridge 20 as measured in the radial direction of the support 122. Accordingly, the cartridge 20 is permitted to move in the cartridge holding portion 122a in the circumferential direction of the support 122 by a limited distance while it cannot move in the radial direction.

Figure 6:
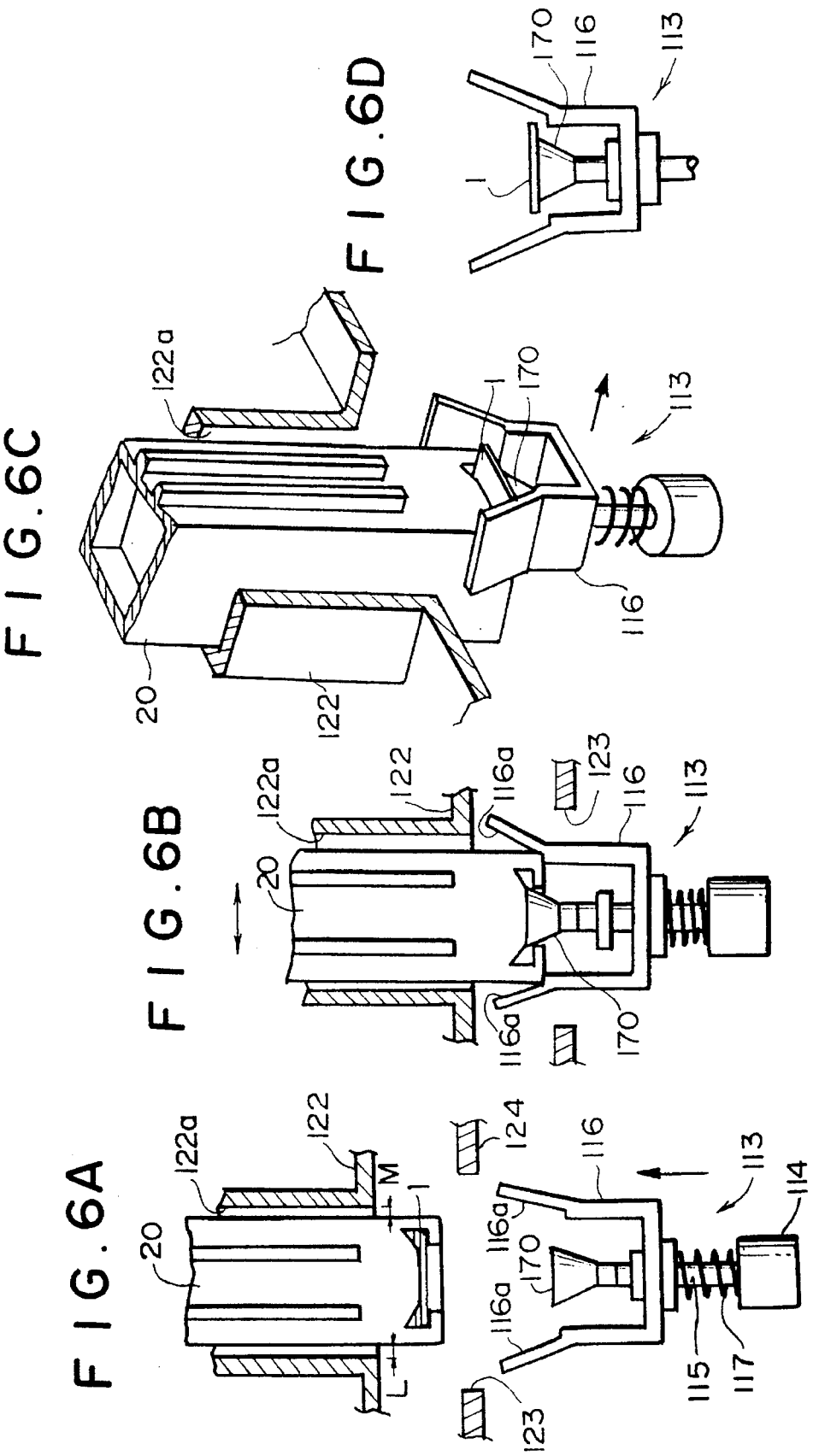

When a desired cartridge 20 is stopped in the film takeout position opposed to the film takeout port 123 and the film takeout port 123 is opened as shown in FIG. 6A, the film takeout means 113 is moved right upward into the film supplier 111 through the film takeout port 123 as shown in FIG. 6B. The guide member 116 has a pair of guide surfaces 116a which flare upward. One edge of the bottom of the cartridge 20 is brought into abutment against one of the guide surfaces 116a as the film takeout means 113 moves upward, and as the film takeout means 113 moves further upward, the edge of the bottom of the cartridge 20 slides along the guide surface 116a, whereby the cartridge 20 can be properly positioned relative to the suction pad 170 as shown in FIG. 6B.

Then the suction pad 170 is inserted into the cartridge 20 through the second opening 20e and brought into a close contact with the lowermost film 1 in the cartridge 20. The suction pad 170 holds the lowermost film 1 under a suction force and slides it radially inwardly, thereby taking out the chemical analysis film 1 from the cartridge 20 as shown in FIG. 6C. Then the film 1 is conveyed out through the film takeout port 123 being held by the suction pad 170 as shown in FIG. 6D.

Another concrete embodiment of the chemical analysis film supplier will be described with reference to FIGS. 7 and 8, hereinbelow.

Figure 7:
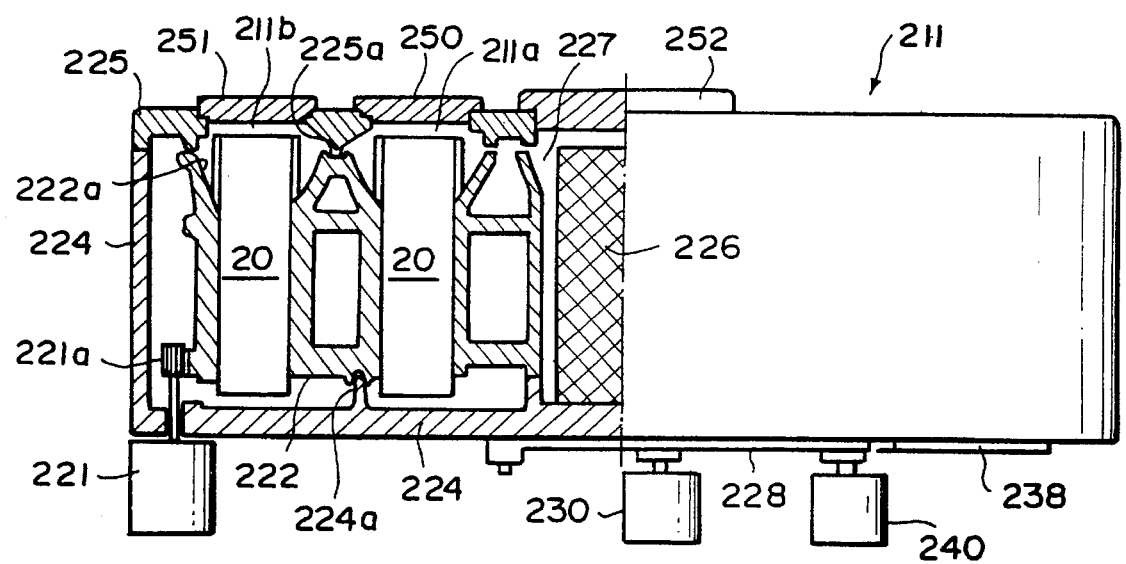
FIG. 7 is a schematic cross-sectional view showing a film supplier in accordance with another embodiment of the present invention.
Figure 8:
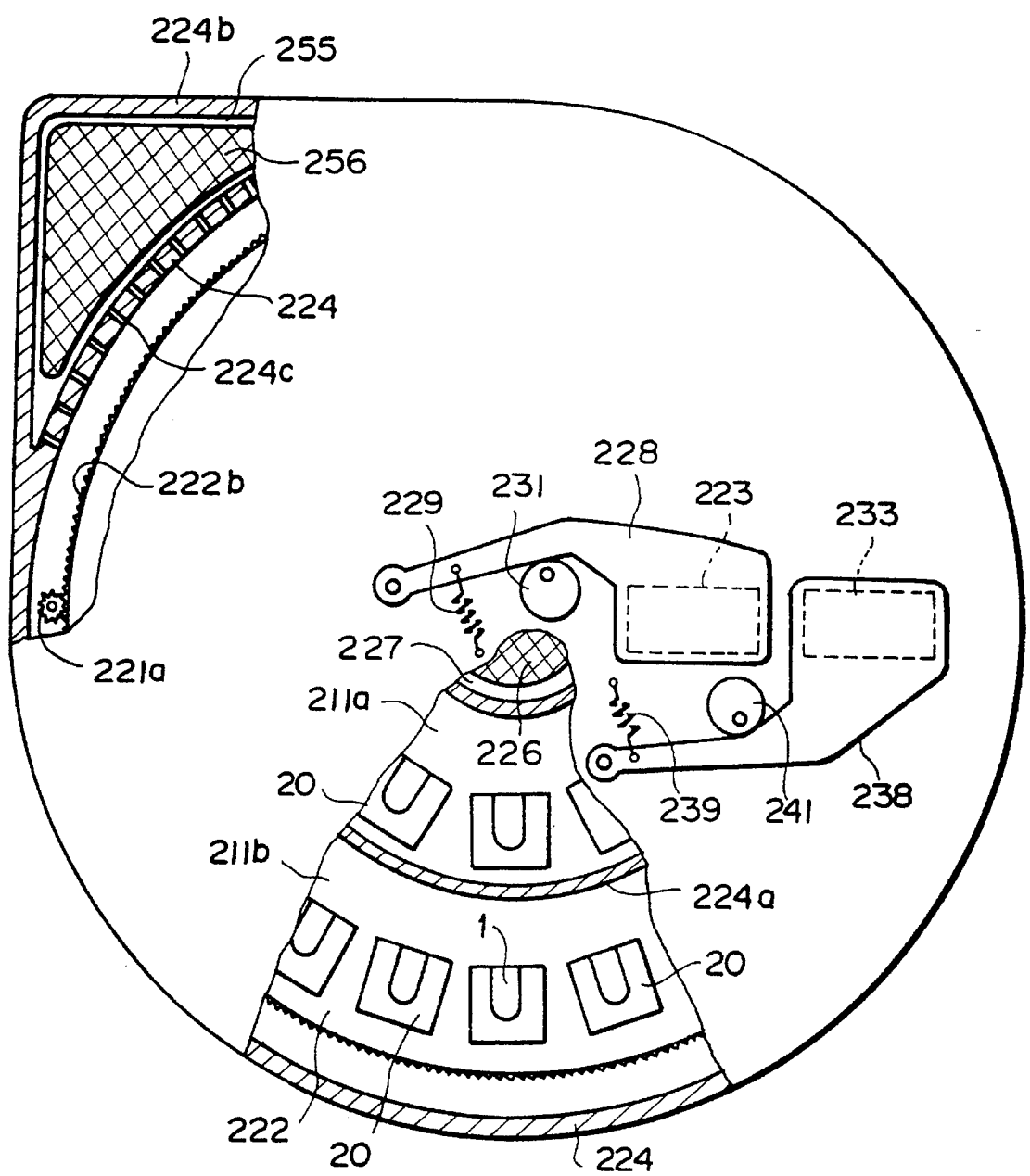
FIG. 8 is a bottom view partly cut away of the film supplier shown in FIG. 7.

In the chemical analysis film supplier 211 shown in FIGS. 7 and 8, the cartridge holding portions 222a are arranged in inner and outer circles and the film storage chambers are partitioned into inner and outer chambers 211a and 211b. The inner and outer chambers 211a and 211b are respectively provided with moisture-absorptive agents 226 and 256 so that the chemical analysis films 1 in the respective chambers can be stored under different humidity conditions.

That is, in the film supplier 211, a support 222 is supported for rotation in a base portion 224 which is closed by a cover 225. Gear teeth 222b are formed on the peripheral surface of the support 222 and are in mesh with a gear 221a driven by a support motor 221 so that the support 222 is rotated to a desired position by the support motor 221. The cartridge holding portions 222a are formed in inner and outer concentric circles on the support 222. The cover 225 is provided with inner and outer lids 250 and 251, and the cartridges 20 are inserted into the inner cartridge holding portions 222a through the inner lid 250 and into the outer film holding portions 222a through the outer lid 251.

An annular sealing protrusion 225a is formed on the lower surface of the cover 225 to project downward between the inner and outer cartridge holding portions 222a and the lower edge of the sealing protrusion 225a is positioned near a groove formed on the upper surface of the support 222. Similarly an annular sealing protrusion 224a is formed on the upper surface of the bottom of the base portion 224 to project upward between the inner and outer cartridge holding portions 222a and the upper edge of the sealing protrusion 224a is positioned near a groove formed on the lower surface of the support 222. Thus the inner space of the film supplier 211 is partitioned into inner and outer film storage chambers 211a and 211b. An inner moisture-absorptive agent holding portion 227 is formed at the center of the inner film storage chamber 211a and a first moisture-absorptive agent (moisture conditioning agent) 226 is put in the inner moisture-absorptive agent holding portion 227, whereby the atmosphere in the inner film storage chamber 211a is kept in a predetermined humidity range above 0% RH (e.g., 5 to 20% RH). As clearly shown in FIG. 8, an extension 224b is provided on the periphery of the base portion 224 to form an outer moisture-absorptive agent holding portion 255. Vent holes 224c are formed in the wall portion of the base portion 224 between the outer moisture-absorptive agent holding portion 255 and the outer film storage chamber 211b, whereby circulation of air between the outer moisture-absorptive agent holding portion 255 and the outer film storage chamber 211b is permitted. A second moisture-absorptive agent (moisture conditioning agent) 256 is put in the outer moisture-absorptive agent holding portion 255, whereby the atmosphere in the outer film storage chamber 211a is kept in a predetermined humidity range about 0% RH (e.g., 0 to 10% RH).

A first film takeout port 223 through which the films 1 in the inner film storage chamber 211a are taken out and a second film takeout port 233 through which the films 1 in the outer film storage chamber 211b are taken out are formed in the bottom of the base portion 224. The film takeout ports 223 and 233 are respectively provided with first and second shutters 228 and 238, which are opened respectively by first and second cams 231 and 241 respectively driven by first and second shutter motors 230 and 240 (FIG. 7). The shutters 228 and 238 are closed respectively under the forces of first and second springs 229 and 239.

Though, in the preceding embodiment, the cartridges (cartridge holding portions) are arranged in two circles and the film storage chamber is partitioned into two chambers, the cartridges may be arranged in three or more circles while the film storage chamber is partitioned into two chambers.

A chemical analysis film supplier in accordance with still another embodiment of the present invention will be described with reference to FIGS. 9 to 14, hereinbelow.

Figure 9:
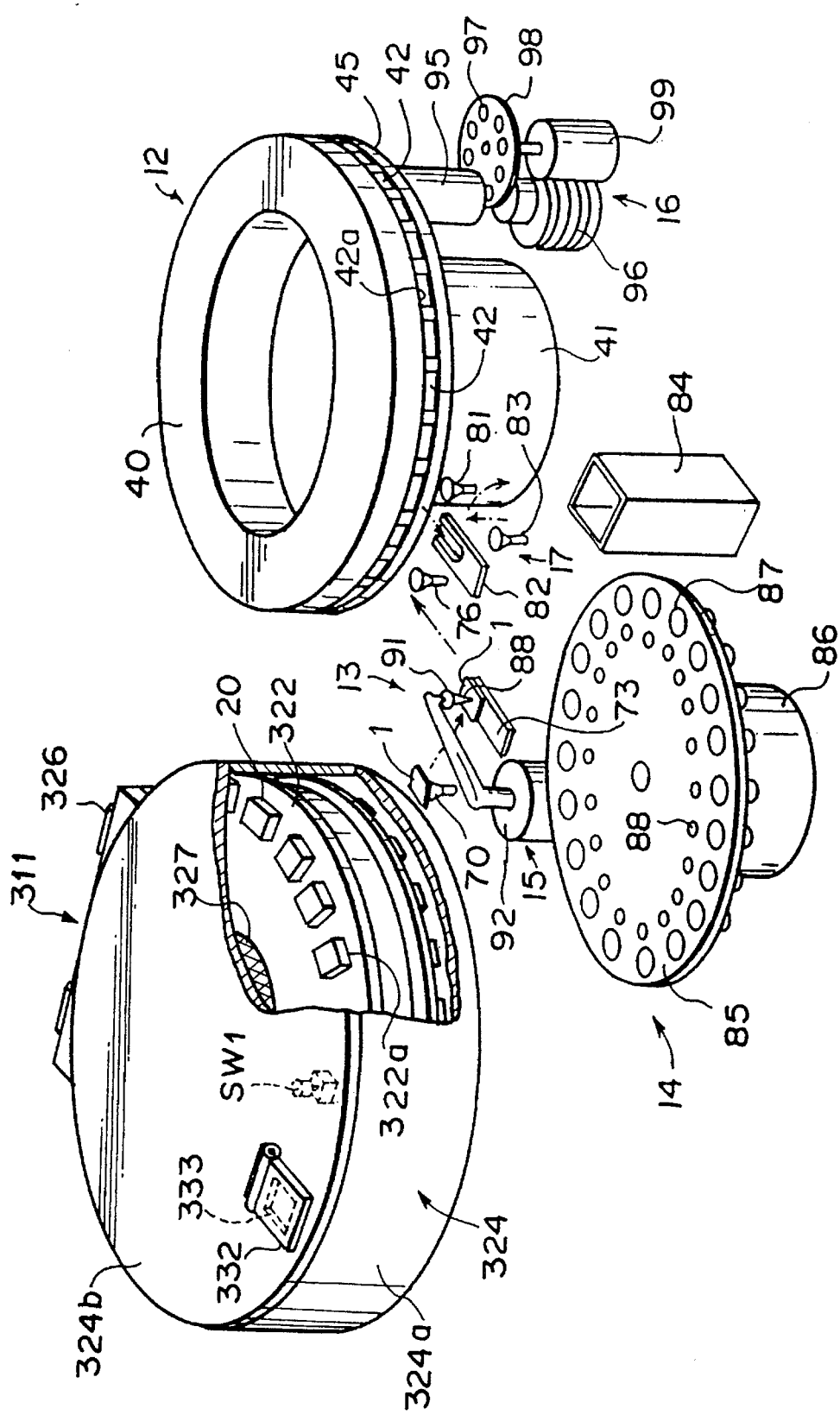
FIG. 9 is a schematic perspective view of a biochemical analysis apparatus provided with a chemical analysis film supplier in accordance with still another embodiment of the present invention.
Figure 10:
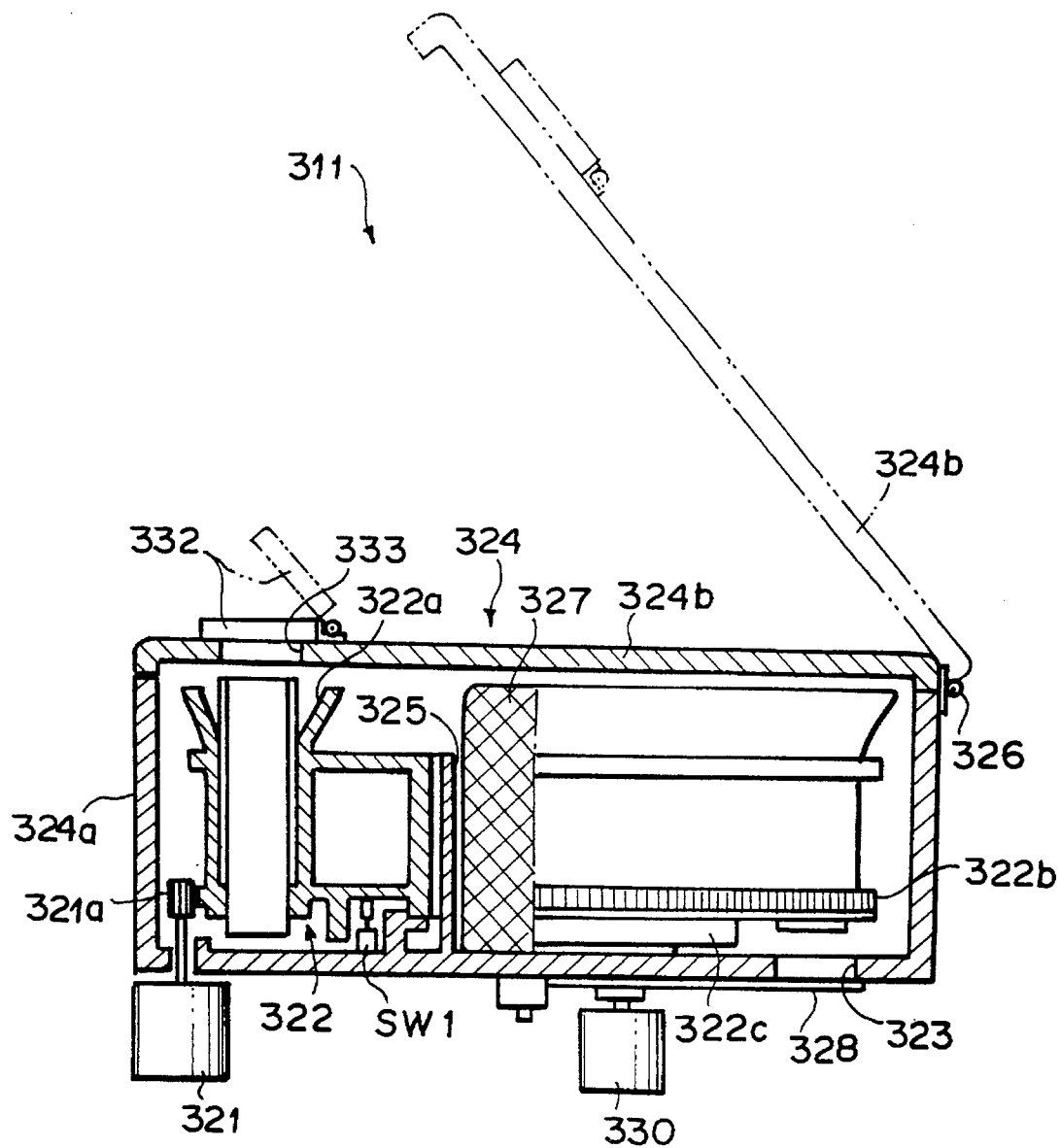
FIG. 10 is a schematic cross-sectional view of the film supplier shown in FIG. 9.
Figure 11:
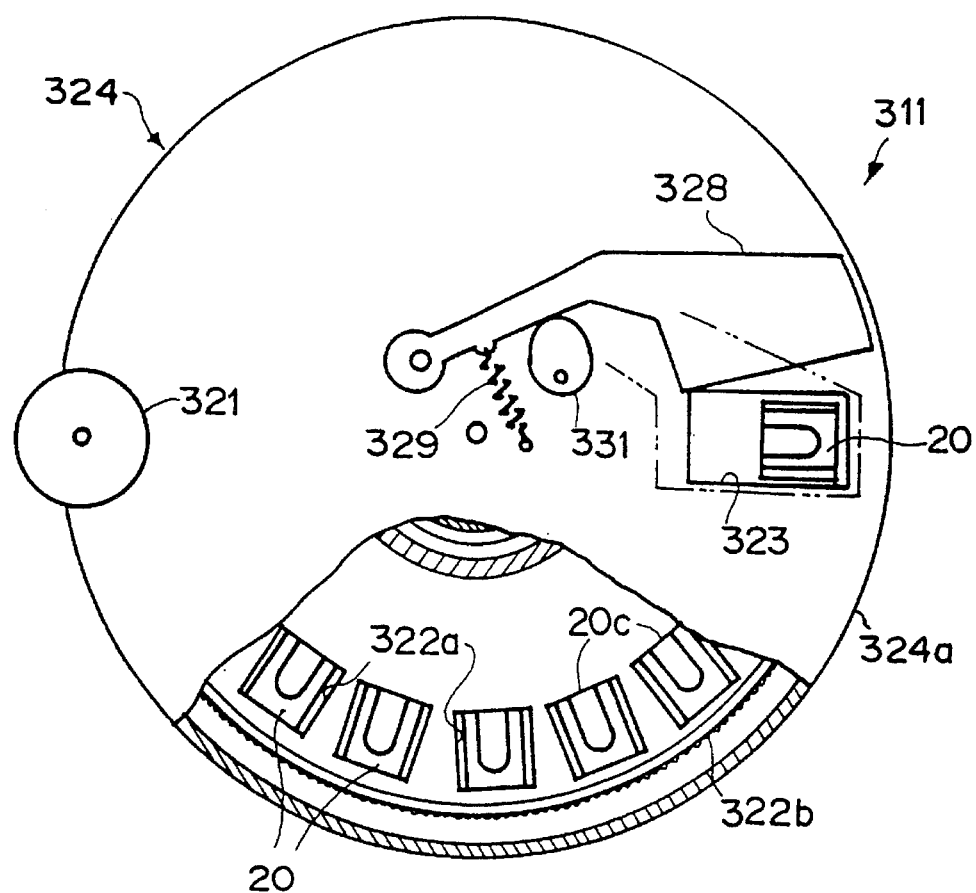
FIG. 11 is a bottom view partly cut away of the film supplier shown in FIG. 9.
Figure 12:
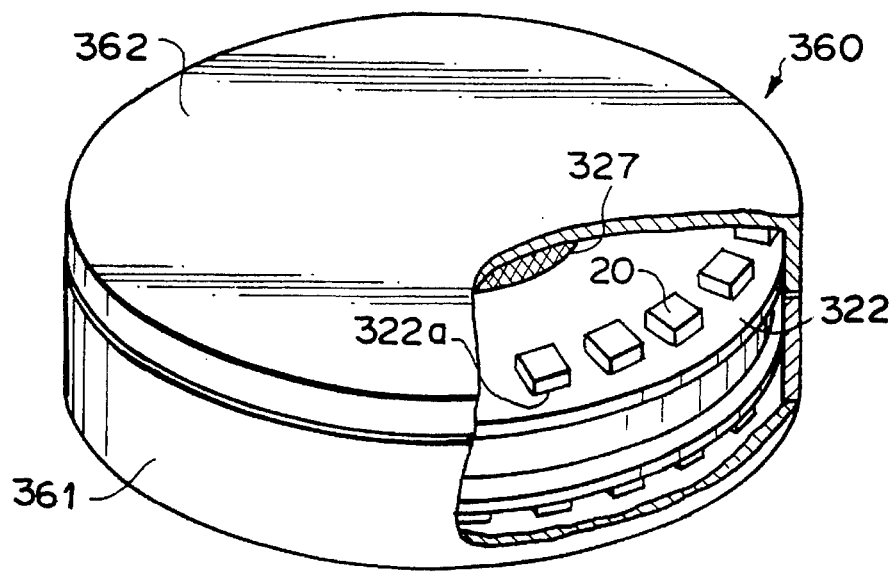
FIG. 12 is a schematic perspective view showing a shelter box.

FIG. 9 shows a chemical analysis apparatus provided with a chemical analysis film supplier in accordance with still another embodiment of the present invention. The apparatus shown in FIG. 9 is substantially the same as that shown in FIG. 1 except the structure of the chemical analysis film supplier and accordingly, the parts analogous to those shown in FIG. 1 are given the same reference numerals and will not be described here. As shown in FIGS. 9 and 10, the film supplier 311 of this embodiment comprises a container 324 and a nest 322 for holding chemical analysis film cartridges 20. The container 324 comprises a container body 324a and a lid 324b and the nest 322 is received in the container body 324a. The lid 324b is connected to the container body 324a by a hinge 326 to be opened and closed and is locked to the container body 324a in the closed position by a lock mechanism (not shown).

The nest 322 is annular in shape and is supported in the container body 324a to be rotatable relative to the container body 324a and to be removable from the container body 324a. The nest 322 is provided with a plurality of cartridge holding portions 322a, and the cartridges 20 are inserted into the cartridge holding portions 322a through a cartridge insertion port 333 formed in the lid 324b. The cartridge insertion port 333 is provided with a door 332.

A cylindrical moisture-absorptive agent holding portion 325 is formed in the container body 324a at the center thereof and a moisture-absorptive agent 327 is loaded in the cylindrical moisture-absorptive agent holding portion 325, whereby the atmosphere in the container 324 is kept at a low humidity. In this embodiment, the lid 324b is opened and the moisture-absorptive agent 327 is changed though an opening for changing the moisture-absorptive agent 327 may be provided in the lid 324b.

A film takeout port 323 for taking out a film 1 from the cartridge 20 is formed in the bottom wall of the container body 324a and a shutter 328 for opening and closing the port 323 is provided. The shutter 328 is urged by a spring 329 toward a closing position in which it closes the port 323 and is driven to an open position where it opens the port 323 by a cam 331 which is rotated by a shutter motor 330.

Teeth 322b are formed on the peripheral surface of the nest 322 and are in mesh with a gear 321a fixed to the output shaft of a nest motor 321. The nest 322 is rotated by the nest motor 321 so that a predetermined one of the cartridge holding portions 322a (i.e., the cartridge therein) is brought to a film takeout position opposed to the film takeout port 323.

When the chemical analysis film supplier 311 fails or is to be maintained, or when the chemical analysis film stored therein is not to be used for a predetermined time interval, the lid 324b is opened and the cartridges 20 are removed from the container body 324a on the nest 322. When the nest 322 is lifted vertically, the teeth 322b on the nest 322 can be easily disengaged from the gear 321a fixed to the output shaft of the nest motor 321. The nest 322 carrying thereon the cartridges 20 is put in a shelter box 360 shown in FIG. 12. As shown in FIG. 10, a spacer portion 322c is formed on the lower surface of the nest 322 in order to space the lower ends of the cartridges 20 from the bottom of the container body 324a when the nest 322 is loaded in the container body 324a. The spacer portion 322c spaces the lower ends of the cartridges 20 from the bottom of the shelter box 360 when the nest 322 is put therein.

A moisture-absorptive agent 327 is put in the shelter box 360 together with the nest 322 in order to keep the atmosphere in the shelter box 360 at a low humidity. The nest 322 is the shelter box 360 is stored in a refrigerator at a low temperature and a low humidity. When the nest 322 is to be returned to the film supplier 311, the shelter box 360 is taken out from the refrigerator and the nest 322 is taken out from the shelter box 360. Then the nest 322 is put into the container body 324a. When the nest 322 is put into the container body 324a, the teeth 322b on the nest 322 are automatically engaged with the gear 321a.

In this particular embodiment, the film supplier 311 is provided with an indicating system which judges whether the cartridges 20 (more strictly the chemical analysis films 1 in the cartridges 20) in the nest 322 returned to the container body 324a are still usable and indicates the result of the judgment.

Figure 13:
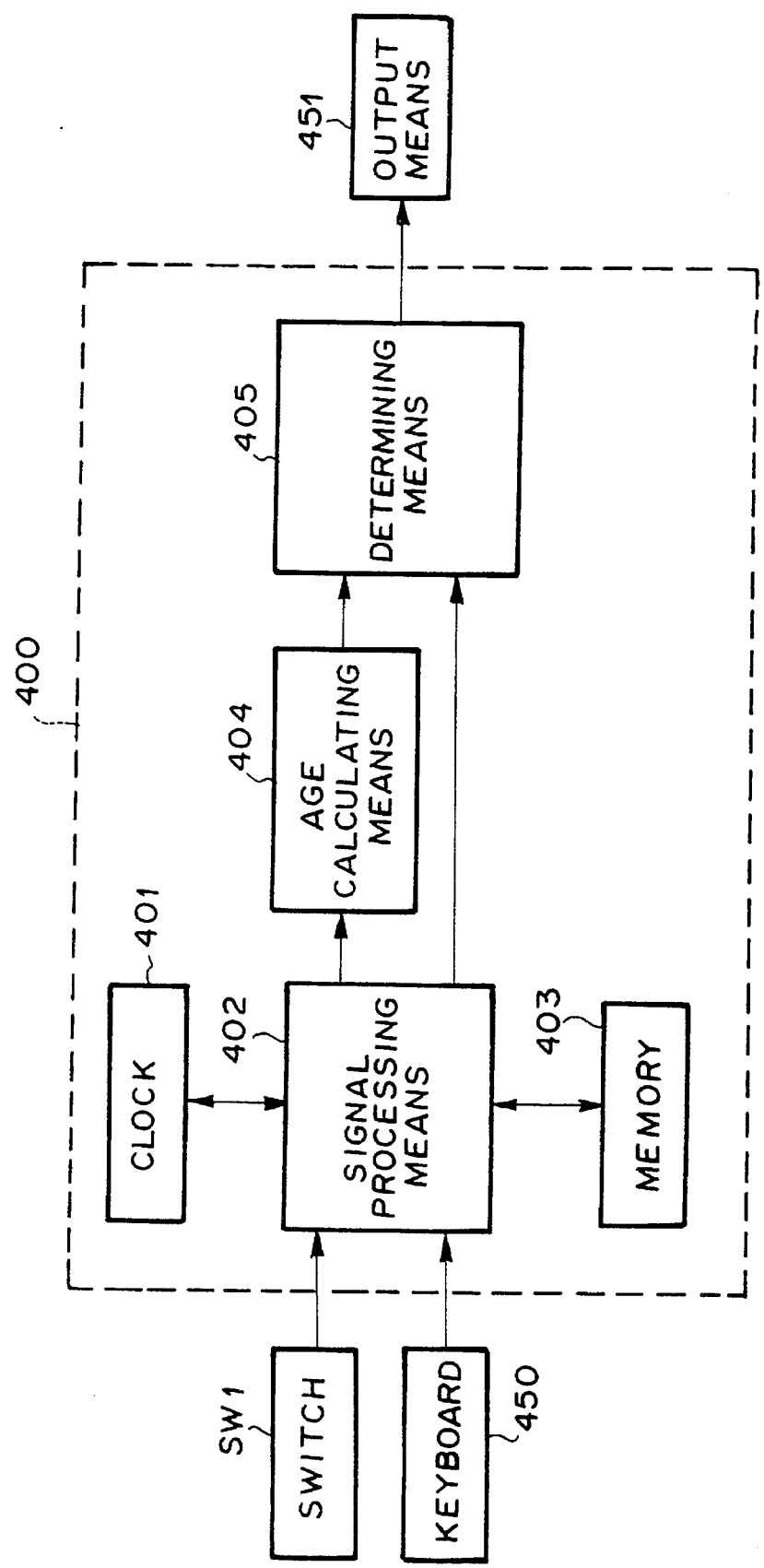
FIG. 13 is a block for illustrating the judging means.

As shown in FIG. 13, the indicating system comprises a control means 400 which may comprise a computer and a switch SW1, a keyboard 450 and an output means 451 which are connected to the control means 400. The output means 451 may comprise a speaker and a CRT (not shown). As shown in FIG. 10, the switch SW1 is mounted on the bottom of the container body 324a to be kept on under the weight of the nest 322 when the nest 322 is in the container body 324a and to be kept off when the nest 322 is not in the container body 324a. A signal processing means 402 in the control means 400 detects whether the switch SW1 is on or off, and reads out from a clock 401 a time the switch SW1 is turned off (the time the nest 322 is taken out from the container body 324a) and a time the switch SW1 is turned on (the time the nest 322 is returned to the container body 324a). The signal processing means 402 stores the times in a memory 403.

The memory 403 may comprise a RAM or the like, and stores various data input from the keyboard 450 as well as the times the switch SW1 is turned off and turned on. For example, the kind of the cartridge held in each cartridge holding portion 322a, the time the cartridge was loaded in the cartridge holding portion 322a, a reference time which is determined in advance for each kind of the cartridge and represents the service life of the cartridge (or in the chemical analysis films therein), and the like are stored in the memory 403. The cartridge holding portions 322a are numbered and the data are stored for the number of each cartridge holding portion 322a. The data are rewritten by the signal processing means 402 each time the cartridge 20 is changed.

The control means 400 further comprises a cartridge age calculating means 404 which calculates the absent time interval from the time the nest 322 is taken out from the container body 324a to the time the nest 322 is returned to the container body 324a and calculates the effective age of the cartridge 20 on the basis of the absent time as will be described in more detail later, and a judging means 405 which judges whether the chemical analysis films 1 in each cartridge 20 are still usable on the basis of comparison of the reference time and the effective age of the cartridge 20 (i.e., the chemical analysis films 1 therein) which is determined taking into account the absent time and the condition under which the cartridge is stored during the absence.

Figure 14:
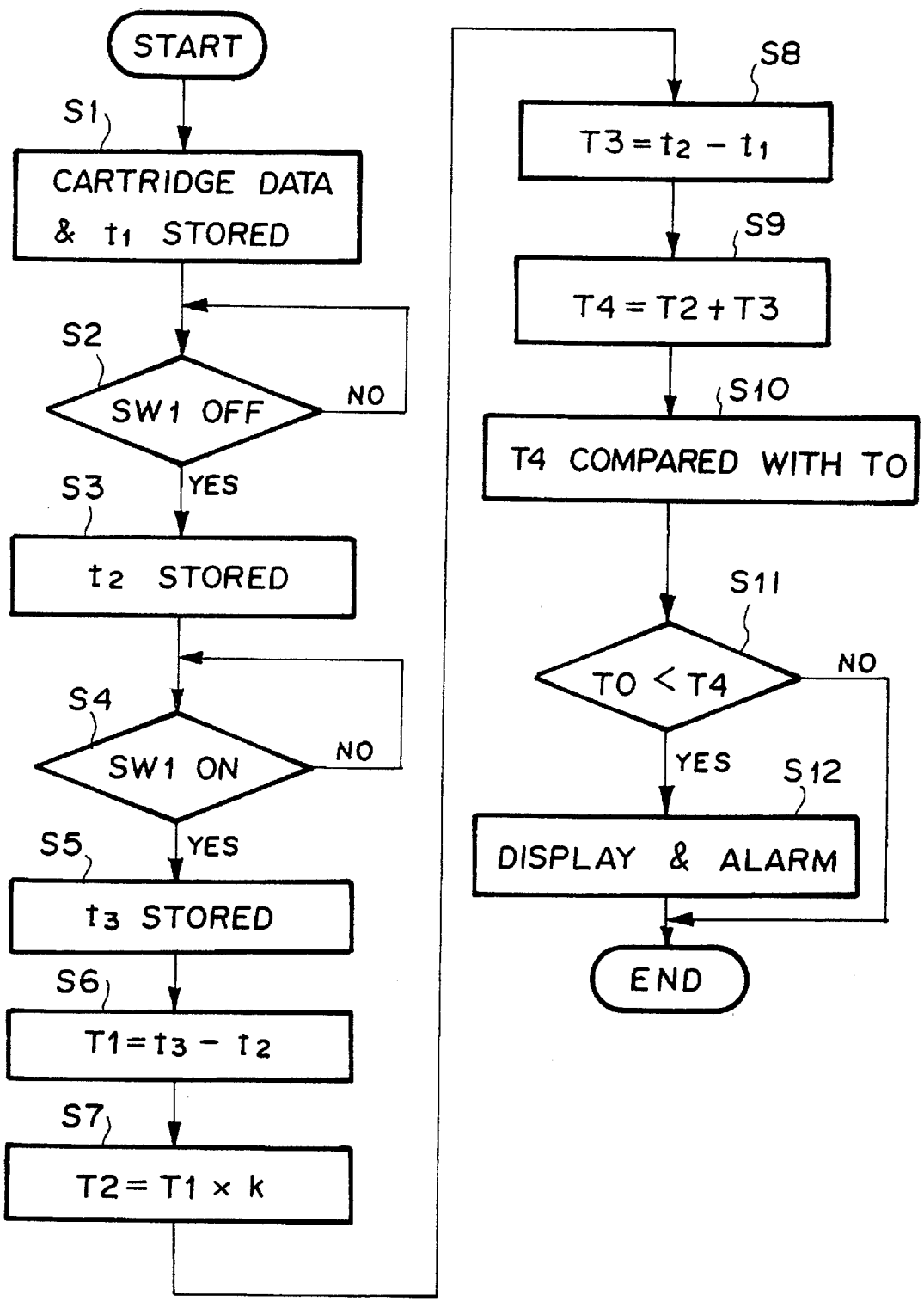
FIG. 14 is a flow chart for judgment of whether the chemical analysis films in each cartridge are still usable.

An example of judgment of whether the chemical analysis films 1 in each cartridge 20 are still usable will be described with reference to the flow chart shown in FIG. 14, hereinbelow.

The numbers of the cartridge holding portions 322a loaded with the cartridges 20 and the kinds of the cartridges 20 loaded are input into the signal processing means 402 by way of the keyboard 450, and the signal processing means 402 stores these data in the memory 403. At the same time, the signal processing means 402 reads out the times $t_1$ the cartridges 20 are loaded from the clock 401 and stores the times in the memory 403. (step S1) Reference times $T_0$ and correction values k for calculating effective ages of the chemical analysis films 1 in the cartridges 20 (to be described later) are stored in the memory for each kind of the cartridge 20.

Then the signal processing means 402 determines whether the switch SW1 turns off (step S2), and when the switch SW1 is turned off, the signal processing means 402 reads out, from the clock 401, the time $t_2$ the switch SW1 is turned off (i.e., the time the nest 322 is taken out from the container 324) and stores the time $t_2$ in the memory 403 (step S3). When the switch SW1 is subsequently turned on, the signal processing means 402 reads out, from the clock 401, the time $t_3$ the switch SW1 is turned on (i.e., the time the nest 322 is returned to the container 324) and stores the time $t_3$ in the memory 403 (steps S4 and S5).

Then the cartridge age calculating means 404 calculates the absent time $T_1$ (for which the nest 322 is absent from the container 324) on the basis of the time $t_2$ the switch SW1 is turned off and the time $t_3$ the switch SW1 is turned on read out from the memory 403 by the signal processing means 402 ($T_1=t_3-t_2$). (step S6) Then the cartridge age calculating means 404 converts the absent time $T_1$ into an effective aging period $T_2$ for each cartridge 20 on the basis of the correction value stored in the memory 403. (step S7) In this particular embodiment, whether the cartridge 20 or the chemical analysis film 1 therein is still usable is judged on the basis of the age of the cartridge 20, i.e., the time which elapses from the time the cartridge 20 is first put in the container 324, and the age of the cartridge 20 is determined taking into account the condition under which the cartridge is kept. That is, the service life of each cartridge 20 is determined in advance in terms of the period for which the cartridge 20 (or the chemical analysis films 1 therein) will be usable when the cartridge 20 is kept in the container 324 throughout its life. Said reference time $T_0$ is determined on basis of the service life of each cartridge 20. Accordingly, when the cartridge 20 is once taken out from the container 324 and is kept under a condition different from the condition in the container 324, the age of the cartridge 20 must be expressed in terms of the age when the cartridge 20 is kept in the container 324 (effective age). For this purpose, the absent time $T_1$ is converted into an effective aging period $T_2$ on the basis of the correction value k. The correction value k for each cartridge 20 is determined on the basis of the difference between the rate of deterioration with age of the chemical analysis films 1 in each cartridge 20 when the cartridge 20 is kept in the container 324 and that when the cartridge 20 is kept under a different condition such as in a refrigerator.

Then in step S8, the cartridge age calculating means 404 calculates the time $T_3$ for which each cartridge 20 is kept in the container 324 before the cartridge 20 is taken out therefrom on the basis of the time $t_2$ the switch SW1 is turned off and the time $t_1$ the cartridge 20 is loaded in the container 324 ($T_3=t_2-t_1$). Then the cartridge age calculating means 404 calculates the effective age $T_4$ of the cartridge 20 on the basis of the time $T_3$ and the effective aging period $T_2$ ($T_4=T_2+T_3$). (step S9)

Then the judging means 405 compares the effective ages $T_4$ of the respective cartridges 20 with the reference times $T_0$ stored in the memory 403 for the kinds of the cartridges 20 and judges whether there is a cartridge 20 whose effective age $T_4$ exceeds the reference time $T_0$ for the kind of the cartridge 20. (steps S10 and S11) When it is determined in step S11 that the effective ages $T_4$ of some of the cartridges 20 exceed the respective reference times $T_0$, the judging means 405 causes the CRT (output means 451) to display the number(s) of the cartridge holding portion(s) 322a corresponding to the cartridge(s) 20 whose effective age(s) $T_4$ exceeds the reference times $T_0$ and causes the speaker to generate an alarm sound. (step S12) When When it is determined in step S11 that the effective age $T_4$ of none of the cartridges 20 exceeds the reference time $T_0$, that is, when all the cartridges 20 are usable, they are used as they are.

The judging means 405 may be arranged to cause the CRT to display the number of the cartridge holding portion carrying a cartridge 20 whose remainder of the service life (i.e., $T_0-T_4$) is shorter than a predetermined time and to cause the speaker to generate an alarm sound when the remainders of the service life of some of the cartridges 20 become shorter than the predetermined time.

Assuming that the deterioration with age of the chemical analysis films 1 is negligible so long as the films 1 are stored in the container 324, whether the cartridge 20 is still usable may be judged solely on the basis of the absent time $T_1$ and the condition under which the cartridge is stored during the absence.

The chemical analysis supplier of the present invention can be applied to not only the frameless dry chemical analysis films but also the dry chemical analysis films with a frame (chemical analysis slides), the dry chemical analysis elements formed of filter paper and the like.

What is claimed is;

1. A chemical analysis film supplier for a biochemical analysis apparatus, comprising:

a film holding member which holds a plurality of dry chemical analysis films in a plurality of film holding portions formed therein;

a container which stores the film holding member therein so that the chemical analysis films can be taken out from each film holding portion, the film holding member is able to be removed from the container and to be returned to the container while carrying thereon the chemical analysis films held in the film holding portions;

absent time calculating means which calculates an absent time from the time the film holding member is taken out from the container to the time the film holding member is returned to the container;

judging means which compares the absent time with a preset reference time and judges whether the chemical analysis films held in the film holding member are still usable on the basis of the result of the comparison; and output means which outputs the result of the judgment by the judging means.

2. A chemical analysis film supplier as defined in claim 1 in which said reference time is set according to a service life of the chemical analysis films for which the chemical analysis films is expected to be usable when the chemical analysis films are kept in the container throughout the life thereof, an age calculating means calculates an effective age of a chemical analysis films held in a film holding member by correcting said absent time on the basis of a correction value which is determined on the basis of the difference between the rate of deterioration with age of the chemical analysis films in the atmosphere in the container and that in the atmosphere in which the chemical analysis films are stored during the absence, and said judging means compares the effective age of the chemical analysis films with said preset reference time and judges whether the chemical analysis films held in the film holding member are still usable on the basis of the result of the comparison.

3. A chemical analysis film supplier as defined in claim 2 in which said age calculating means calculates the effective age of the chemical analysis films held in the film holding member by correcting said absent time on the basis of said correction value and adding, to the corrected absent time, the time for which the chemical analysis films are stored in the container before the film holding member is taken out from the container.

4. A chemical analysis film supplier as claimed in claim 1, wherein the film holding member can be moved relative to the container to bring the chemical analysis films held in each film holding portion to a film takeout port formed in the container; and a driving mechanism for moving the film holding member is arranged to be disengaged from the film holding member when the film holding member is removed from the container and to be engaged with the film holding member when the film holding member is loaded in the container so that the film holding member can be driven.

5. A chemical analysis film supplier as defined in claim 4 in which said reference time is set according to a service life of the chemical analysis films for which the chemical analysis films is expected to be usable when the chemical analysis films are kept in the container throughout the life thereof, an age calculating means calculates an effective age of the chemical analysis films held in the film holding member by correcting said absent time on the basis of a correction value which is determined on the basis of a difference between a rate of deterioration with age of the chemical analysis films in the atmosphere in the container and that in the atmosphere in which the chemical analysis films are stored during the absence, and said judging means compares the effective age of the chemical analysis films with said preset reference time and judges whether the chemical analysis films held in the film holding member are still usable on the basis of the result of the comparison.

6. A chemical analysis film supplier as defined in claim 5 in which said age calculating means calculates the effective age of the chemical analysis films held in the film holding member by correcting said absent time on the basis of said correction value and adding, to the corrected absent time, the time for which the chemical analysis films are stored in the container before the film holding member is taken out from the container.

* * * * *